(12) United States Patent
Guo et al.

(10) Patent No.: US 10,435,736 B2
(45) Date of Patent: Oct. 8, 2019

(54) TARGET REGION ENRICHMENT METHOD BASED ON MULTIPLEX PCR, AND REAGENT

(71) Applicants: BGI SHENZHEN, Shenzhen (CN); BGI SHENZHEN CO., LIMITED, Shenzhen (CN)

(72) Inventors: Jing Guo, Shenzhen (CN); Rongrong Guo, Shenzhen (CN); Meiyan Li, Shenzhen (CN); Chunyu Geng, Shenzhen (CN); Hui Jiang, Shenzhen (CN)

(73) Assignee: MGI TECH CO., LTD., Shenzhen, Guangdong (CN)

( * ) Notice: Subject to any disclaimer, the term of this patent is extended or adjusted under 35 U.S.C. 154(b) by 38 days.

(21) Appl. No.: 15/537,396

(22) PCT Filed: Dec. 9, 2015

(86) PCT No.: PCT/CN2015/096790
§ 371 (c)(1),
(2) Date: Jun. 16, 2017

(87) PCT Pub. No.: WO2016/095736
PCT Pub. Date: Jun. 23, 2016

(65) Prior Publication Data
US 2018/0163251 A1   Jun. 14, 2018

(30) Foreign Application Priority Data

Dec. 18, 2014   (CN) .......................... 2014 1 0796113

(51) Int. Cl.
*C12Q 1/68* (2018.01)
*C12P 19/34* (2006.01)
(Continued)

(52) U.S. Cl.
CPC ............ *C12Q 1/6806* (2013.01); *C12P 19/34* (2013.01); *C12Q 1/6855* (2013.01)

(58) Field of Classification Search
None
See application file for complete search history.

(56) References Cited

U.S. PATENT DOCUMENTS 5,876,932 A * 3/1999 Fischer ................ C12Q 1/6809
                                                      435/6.1
2009/0203002 A1   8/2009 Brown
(Continued)

FOREIGN PATENT DOCUMENTS

CN   101421410 A   4/2009
CN   101815792 A   8/2010
(Continued)

OTHER PUBLICATIONS

International Search Report for PCT/CN2015/096790, dated Mar. 4, 2016, and its English translation provided by WIPO.
(Continued)

*Primary Examiner* — Young J Kim
(74) *Attorney, Agent, or Firm* — Ladas & Parry, LLP (57) ABSTRACT

Provided are a target region enrichment method based on multiplex PCR, and a reagent, the method comprising: connecting a first linker and a second linker respectively at two ends of a nucleic acid segment containing target regions to be enriched so as to obtain a linker-connected product; performing a PCR amplification on the linker-connected product using a first primer specifically bound to the first linker and a second primer specifically bound to the second linker to obtain an amplified product, the first primer or the second primer having a first affinity label; capturing a single strand having the first affinity label in the amplified product using a solid phase carrier; performing single primer linear amplification using a third primer with the captured single strand as a template; performing exponential amplification
(Continued)

using the third primer and the first primer, with the linearly amplified product as the template, to obtain a product containing the target regions.

4 Claims, 1 Drawing Sheet

Specification includes a Sequence Listing.

(51) Int. Cl.
*C12Q 1/6806* (2018.01)
*C12Q 1/6855* (2018.01)

(56) References Cited

U.S. PATENT DOCUMENTS

2010/0240549 A1* 9/2010 Brown ............... C12Q 1/6827
506/9
2013/0231253 A1* 9/2013 Amorese ............ C12N 15/1068
506/2
2014/0249038 A1 9/2014 Jiang et al.

FOREIGN PATENT DOCUMENTS

| CN | 102329876 A | 1/2012 |
| CN | 102533985 A | 7/2012 |
| CN | 102628082 A | 8/2012 |

OTHER PUBLICATIONS

Written Opinion of the International Search Authority for PCT/CN2015/096790, dated Mar. 4, 2016, and its English translation provided by Bing.Com Microsoft Translator.

* cited by examiner

TARGET REGION ENRICHMENT METHOD BASED ON MULTIPLEX PCR, AND REAGENT

CROSS REFERENCE TO RELATED APPLICATIONS

The present application is the U.S. national phase of PCT Application PCT/CN2015/096790 filed on Dec. 9, 2015, which claims priority to the Chinese patent application number 201410796113.7 filed on Dec. 18, 2014, the disclosures of which are incorporated herein by reference in their entireties.

TECHNICAL FIELD

The present invention relates to the field of molecular biology, particularly to a method and a reagent for enriching for a target region based on multiplex PCR.

BACKGROUND OF THE INVENTION

With the development of DNA sequencing technologies, high-throughput sequencing technologies have been widely applied in various fields of life science research. Although the cost of sequencing technologies is becoming lower and lower with the on-going updating and popularization of sequencing technologies, the expense of whole-genome sequencing technologies per se is still costly. A preferable solution to this problem would be to enrich for a target region of interest before conducting high-throughput sequencing. Conventional sequence capture techniques typically involve constructing a high-throughput sequencing library, then enriching the library for a target region using a probe prior to conducting sequencing.

Additionally, Life Tech Corporation developed a kit called Ampliseq based on multiplex PCR technology. The kit allows to achieve enrichment of a target region through a multiplex PCR process, thus greatly shortening the time-consuming operation process of capture by hybridization. This represents an innovation in region capture technology.

However, Ampliseq is unable to enrich for a target region in a cellular free DNA, because the cellular free DNA is characterized by small fragment length, which may even be smaller than the length of the PCR products in the Ampliseq kit. Moreover, the region capture technology based on Ampliseq can achieve pooling of samples only after performing PCR, which would be a time-consuming process.

SUMMARY OF THE INVENTION

The present invention provides a method and a reagent for enriching for a target region based on multiplex PCR, which can achieve capture of a region in a short fragment such as a cellular free DNA and greatly reduce the time and the cost for capturing the region.

According to a first aspect of the present invention, there is provided a method for enriching for a target region based on multiplex PCR, comprising the following steps:

connecting a first linker and a second linker respectively to a terminal end of a nucleic acid fragment comprising a target region to be enriched under the action of a ligase to obtain a linker-connected product, wherein the first linker comprises a fixed sequence of the first linker for subsequent PCR amplification, a first tag sequence for labeling a distinct sample and a second tag sequence for labeling a distinct target molecular sequence;

PCR amplifying the linker-connected product with a first primer that specifically binds to the fixed sequence of the first linker and a second primer that specifically binds to the second linker to obtain an amplification product, wherein the first primer or the second primer has a first affinity label;

capturing a single strand of the amplification product harboring the first affinity label via a solid-phase support, wherein the solid-phase support carries a second affinity label capable of affinity binding to the first affinity label;

performing single-primer linear amplification with a third primer using the captured single strand as template, wherein the third primer comprises a fixed sequence of the third primer at the 5' end and a target-region-specifically-binding sequence at the 3' end; and performing exponential amplification with the third primer and the first primer using a linear amplification product as template to obtain a product comprising the target region.

In a preferred embodiment of the present invention, the first tag sequence is a sequence with a length of 5 to 10 bases, and the second tag sequence is a random sequence with a length of 10 to 12 bases.

In a preferred embodiment of the present invention, the nucleic acid fragment comprising the target region to be enriched is a nucleic acid fragment having been end repaired.

In a preferred embodiment of the present invention, the first primer has the first affinity label.

In a preferred embodiment of the present invention, the first affinity label is a biotin label, the second affinity label is a streptavidin label, and the solid-phase support is a magnetic bead.

According to a second aspect of the present invention, there is provided a reagent for enriching for a target region based on multiplex PCR, comprising the following components:

a first linker and a second linker for respectively connecting to a terminal end of a nucleic acid fragment comprising a target region to be enriched under the action of a ligase to obtain a linker-connected product, wherein the first linker comprises a fixed sequence of the first linker for subsequent PCR amplification, a first tag sequence for labeling a distinct sample and a second tag sequence for labeling a distinct target molecular sequence;

a first primer and a second primer for PCR amplifying the linker-connected product to obtain an amplification product, wherein the first primer specifically binds to the fixed sequence of the first linker, the second primer specifically binds to the second linker, and the first primer or the second primer has a first affinity label;

a solid-phase support for capturing a single strand of the amplification product harboring the first affinity label, wherein the solid-phase support carries a second affinity label capable of affinity binding to the first affinity label;

a third primer for performing single-primer linear amplification using the captured single strand as template, wherein the third primer comprises a fixed sequence of the third primer at the 5' end and a target-region-specifically-binding sequence at the 3' end; and wherein the third primer and the first primer are also used for performing exponential amplification using a linear amplification product as template to obtain a product comprising the target region.

In a preferred embodiment of the present invention, the first tag sequence is a sequence with a length of 5 to 10 bases, and the second tag sequence is a random sequence with a length of 10 to 12 bases.

In a preferred embodiment of the present invention, the nucleic acid fragment comprising the target region to be enriched is a nucleic acid fragment having been end repaired.

In a preferred embodiment of the present invention, the first primer has the first affinity label.

In a preferred embodiment of the present invention, the first affinity label is a biotin label, the second affinity label is a streptavidin label, and the solid-phase carrier is a magnetic bead.

In the method for enriching for a target region based on multiplex PCR according to the present invention, a product connected with a tag sequence is first subjected to linear amplification to enrich for a target region, then the target region is subjected to PCR enrichment using a particular primer (third primer). Thus, short nucleic acid fragments no longer constitute a limitation to multiplex PCR, and capturing of a region in a short fragment such as a cellular free DNA can be achieved. Pooling of multiple samples can be achieved prior to enriching the product connected with a particular tag sequence (first tag sequence) for the target region, which greatly reduces the cost of sample treatment and increases the throughput of sample treatment.

Moreover, in the present invention, besides labeling a distinct sample with a distinct tag (first tag sequence), molecules derived from different target regions in the same sample are also labelled with multiple molecular tags (second tag sequence). The multiple molecular tags allow to differentiate the same molecules in respect of whether they are generated from PCR amplification. Thus, a molecular sequence with a low mutation rate (such as, a mutation rate of one thousandth) and a normal sequence can be discriminated in a high-depth sequencing, which facilitates screening and study of a sample with a low mutation rate.

DETAILED DESCRIPTION OF THE INVENTION

The present invention is described in further detail below by reference to particular embodiments. Unless otherwise stated, the techniques used in the following embodiments are all conventional techniques known to a person skilled in the art, and the instruments, equipments and reagents used are all publicly available, e.g. commercially available, to a person skilled in the art.

In the present invention, the concepts of "first", "second" and "third" used in any cases should not be construed as conveying the meaning of order or technique, and they serve only to distinguish the objects to which they refer from other objects.

Figure 1:
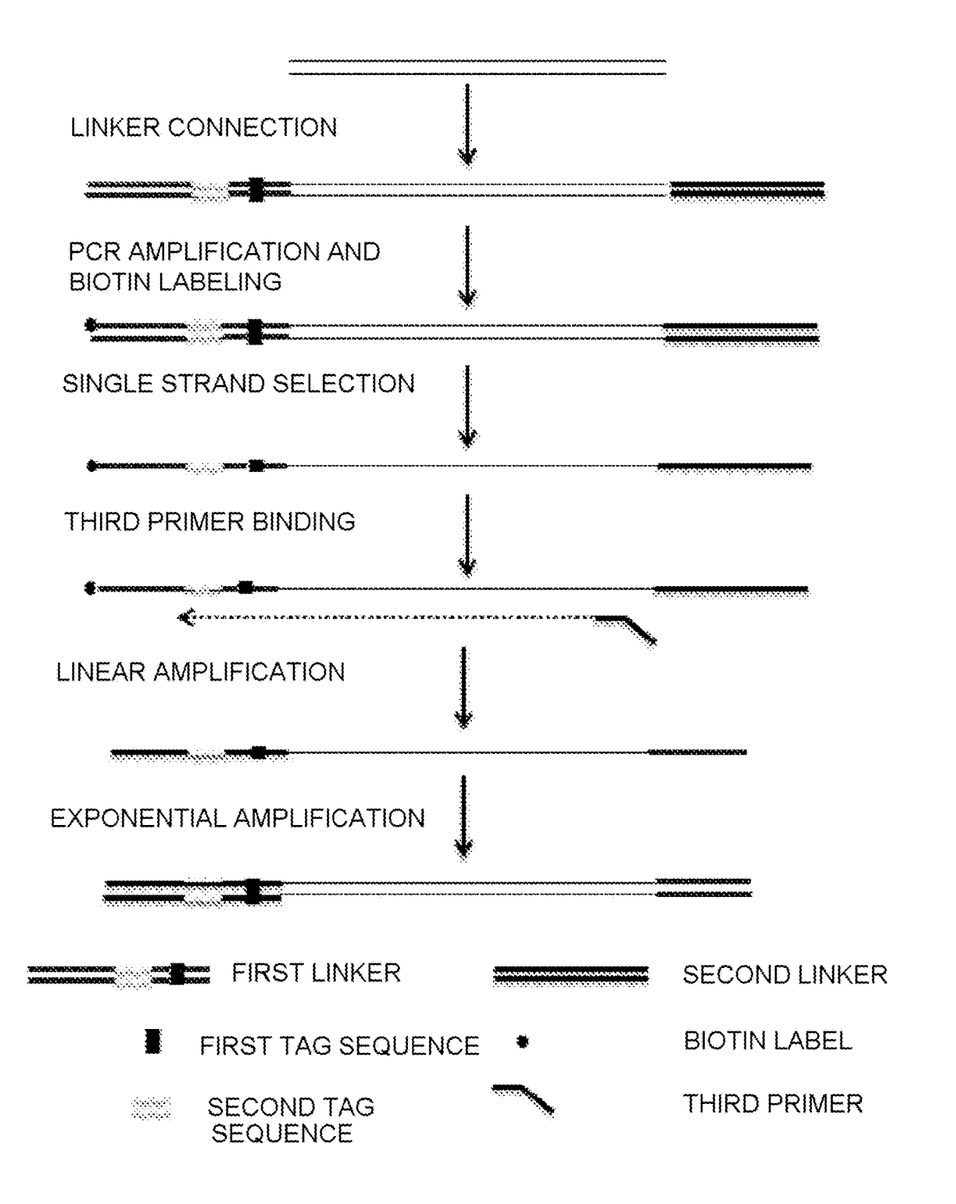
FIG. 1 is a schematic diagram showing the principle underlying an embodiment of the method for enriching for a target region based on multiplex PCR according to the present invention.

Referring to FIG. 1, in an embodiment of the present invention, the method for enriching for a target region based on multiplex PCR mainly comprises the following steps: linker connection; PCR amplification and biotin labeling; single strand selection; third primer binding; linear amplification; and exponential amplification. The steps are described in specific detail below.

Linker connection involves connecting a first linker and a second linker respectively to a terminal end of a nucleic acid fragment comprising a target region to be enriched under the action of a ligase to obtain a linker-connected product, wherein the first linker comprises a fixed sequence of the first linker for subsequent PCR amplification, a first tag sequence for labeling a distinct sample and a second tag sequence for labeling a distinct target molecular sequence.

The above-said nucleic acid fragment can be a nucleic acid fragment from any source comprising the target region to be enriched, typical but not limitative examples thereof including: a random fragment obtained from a genomic DNA via physical disruption or disruption by a transposase embedment complex, a PCR amplification product, a whole genome amplification (WGA) product, and the like. In particular, a short fragment molecule such as a cellular free DNA can also be used as the nucleic acid fragment in the present invention for enriching for a target region.

The nucleic acid fragment generated by the above-said method may need to be end repaired. This is the case especially for the nucleic acid fragment generated by physical disruption, which needs to be subjected to end filling using a DNA polymerase and to phosphorylation treatment using a DNA phosphorylation kinase, so as to facilitate subsequent linker connection reaction.

The first linker and the second linker are both short double-stranded nucleotide sequences, ranging from ten-odd base pairs to several tens of base pairs in length.

With respect to the first linker, the fixed sequence of the first linker is at the 5' end of the sequence and is used for subsequent PCR amplification, that is, used as a primer annealing site for subsequent PCR amplification; and the first tag sequence and the second tag sequence are downstream (i.e., at the 3' end) of the fixed sequence of the first linker. There is no limitation to the sequence (or position) of the first tag sequence and the second tag sequence, that is, the first tag sequence can be upstream (i.e. at the 5' end) or downstream (i.e., at the 3' end) of the second tag sequence, and vice versa. By "fixed sequence" is meant that such a stretch of sequence is fixed and unchanged, while the sequence of other parts of the first linker may vary. Hence, the concept of "fixed sequence" can also be referred to as "unchanged sequence" or "universal sequence" or the like. Additionally, any two of the fixed sequence of the first linker, the first tag sequence and the second tag sequence adjacent to each other may either be connected directly, or intervened by a few bases, that is, connected via a "connection sequence" to form the first linker.

The first tag sequence is used for labelling a distinct sample. That is, nucleic acid fragments from the same sample source will harbor the same first tag sequence after linker connection, while nucleic acid fragments from different sample sources will harbor a different first tag sequence after linker connection. This allows the present invention to achieve pooling of multiple samples prior to enriching for the target region, in contrast to a conventional method in which pooling of different samples can only be performed after enriching for the target region by PCR, which greatly reduces the cost of sample treatment and increases the throughput of sample treatment.

The second tag sequence is used for labelling a distinct target molecular sequence. That is, the target nucleic acid fragments in the same sample will harbor a different second tag sequence after linker connection. The second tag sequence is a random sequence having a length generally ranging from 10 to 12 bases. Theoretically, a random sequence having N bases will result in $4^N$ types of the second tag sequence, which are sufficient to label millions of target regions. Therefore, the multiple molecular tags of the present invention allow to differentiate the same molecules in respect of whether they are generated from PCR amplification. Thus, a molecular sequence with a low mutation rate (such as, a mutation rate of one thousandth) and a normal sequence can be discriminated in a high-depth sequencing, which facilitates screening and study of a sample with a low mutation rate.

In light of the above, the concepts of first tag sequence and second tag sequence in the present invention do not refer to a sequence stretch having a particular sequence, but refer to a "tag set" which may vary according to the source of the sample and the molecular source of the nucleic acid fragments. Accordingly, the first linker is not a sequence stretch having a particular sequence, but refers to a "linker set". However, the second linker is a sequence stretch having a particular sequence and is universal in the present invention for enriching for a target region by PCR amplification.

While the linker connection step is intended to connect the first linker and the second linker respectively to a terminal end of a nucleic acid fragment comprising a target region to be enriched, there exists the case that both terminal ends of the same nucleic acid fragment are connected with the first linker or the second linker at the same time, due to the possible incapability of selective connection of the first linker and the second linker. This, however, does not affect the effectiveness of the present invention, because the PCR amplification step following linker connection uses a first primer that specifically binds to the fixed sequence of the first linker and a second primer that specifically binds to the second linker, such that those nucleic acid fragments of interest to which the first linker and the second linker are connected at a respective terminal end are enriched. Of course, the connection mode can also be designed in a manner such that the first linker and the second linker is specifically connected to a respective terminal end of the nucleic acid fragment. For example, the connection mode that can be employed may be blunt end connection or sticky end connection. If the first linker and the second linker are respectively connected in a different connection mode, the case that both terminal ends of the same nucleic acid fragment are connected with the same linker can be avoided.

PCR amplification and biotin labeling involves PCR amplifying the linker-connected product with a first primer that specifically binds to the fixed sequence of the first linker and a second primer that specifically binds to the second linker to obtain an amplification product, wherein the first primer or the second primer has a first affinity label.

In an embodiment of the present invention, a biotin is used as the first affinity label to label the first primer or the second primer, and accordingly, a streptavidin is used as the second affinity label to label the solid support. The biotin-streptavidin system represents a biological affinity labelling method which finds the widest use and gives the best results in biology. Of course, the present invention is not limited thereto. The first affinity label may be a component of a biological binding reaction commonly used in biology, such as an antigen or an antibody, one strand of a short double-stranded DNA fragment, a biotin or a streptavidin, and the like. In the case that an antigen is used as the first affinity label, an antibody that binds to the antigen is used as the second affinity label, and vice versa; in the case that one strand of a short double-stranded DNA fragment is used as the first affinity label, another strand that is complementary to the strand is used as the second affinity label, and vice versa; and in the case that a biotin is used as the first affinity label, a streptavidin that binds to the biotin is used as the second affinity label, and vice versa.

In an embodiment of the present invention, the solid support is a magnetic bead. Additionally, a microwell plate, a chip or the like can be used as the solid support, so long as the second affinity label (such as streptavidin) can be attached to the solid support. In the present invention, a magnetic bead is most preferred.

Single strand selection involves capturing a single strand of the amplification product harboring the first affinity label via the solid support, wherein the solid support carries the second affinity label capable of affinity binding to the first affinity label.

In an embodiment of the present invention, the solid support is a magnetic bead, the first affinity label is a biotin label, and the second affinity label is a streptavidin label. Thus, using a streptavidin-labeled magnetic bead and by virtue of binding of streptavidin to biotin, a single strand of the PCR amplification product harboring a biotin label is collected for later use in enrichment operation on downstream target regions.

Third primer binding and linear amplification involves performing single-primer linear amplification with a third primer using the captured single strand as template, wherein the third primer comprises a fixed sequence of the third primer at the 5' end and a target-region-specifically-binding sequence at the 3' end.

In this step, the fixed sequence of the third primer means that such a stretch of sequence is fixed and unchanged, while other parts of the third primer may vary. Hence, the concept of "fixed sequence" can also be referred to as "unchanged sequence" or "universal sequence" or the like. The target-region-specifically-binding sequence at the 3' end of the third primer can specifically bind to a target region to be enriched and achieve enrichment of the target region by PCR amplification.

Exponential amplification involves exponentially amplifying the linear amplication product as template using the third primer and the first primer to obtain a product comprising the target region. Thus, enrichment of the target region is achieved.

The product obtained following enrichment of the target region can be subsequently used in a high-throughput sequencing platform or another analytical platform. The method of the present invention can also be used in various other tissue samples, or even medical samples embedded with paraffin or fixed with formaldehyde.

The present invention is described in more detail below by reference to examples.

In one example, sequences of the linkers and primers used are as shown in Table 1.

TABLE 1

Sequences of linkers and primers

| Name | Sequence | SEQ ID NO: |
|---|---|---|
| First linker | CCATCTCATCCCTGCGTGTCTCCGACTCAGNNNNNNNNNN CTAAGGTAACGAT (sense strand) | 1 |
|  | ATCGTTACCTTAGNNNNNNNNNNCTGAGCGGAGACACGC AGGGATGAGATGGTT (antisense strand) | 2 |
| Second linker | AAGTCGGAGGCCAAGCGGTCTTAGGA (sense strand) | 3 |
|  | TCCTAAGACCGCTTGGCCTCCGACT (antisense strand) | 4 |

TABLE 1-continued

Sequences of linkers and primers

| Name | Sequence | SEQ ID NO: |
|---|---|---|
| First primer | /5-bio/CCATCTCATCCCTGCGTGTC | 5 |
| Second primer | TCCTAAGACCGCTTGGCCTCCGACT | 6 |
| Third primer | CCACTACGCCTCCGCTTTCCTCTCTATGGGCAGTCGGTGA TTTCTATGGTGTGTCCCCAACT | 7 |
|  | CCACTACGCCTCCGCTTTCCTCTCTATGGGCAGTCGGTGA TTGGGAGCCCCGTTCTATATCA | 8 |
|  | CCACTACGCCTCCGCTTTCCTCTCTATGGGCAGTCGGTGA TTGCGCCACAGAGAAGTTGTTGA | 9 |
|  | CCACTACGCCTCCGCTTTCCTCTCTATGGGCAGTCGGTGA TTTCTCTCGGAGGAAGGACTTGAG | 10 |
|  | CCACTACGCCTCCGCTTTCCTCTCTATGGGCAGTCGGTGA TTGAGAGAACGCGGAATTGGTCTA | 11 |
|  | CCACTACGCCTCCGCTTTCCTCTCTATGGGCAGTCGGTGA TTTTCATTATCATCTTTGTCATCAGCTGAA | 12 |
|  | CCACTACGCCTCCGCTTTCCTCTCTATGGGCAGTCGGTGA TTAGCCCCAGTGATCTTCAGATA | 13 |
|  | CCACTACGCCTCCGCTTTCCTCTCTATGGGCAGTCGGTGA TTTTAAATACAGAAGGCATAAATATTCCAGCAGA | 14 |
|  | CCACTACGCCTCCGCTTTCCTCTCTATGGGCAGTCGGTGA TTTGCTATTCTCAGATGACTCTGTGTTTTT | 15 |
|  | CCACTACGCCTCCGCTTTCCTCTCTATGGGCAGTCGGTGA TTGTGTTTGACTCTAGATGCTGTGAGAA | 16 |
|  | CCACTACGCCTCCGCTTTCCTCTCTATGGGCAGTCGGTGA TTGCTCATACAGCAGGCCATAGA | 17 |
|  | CCACTACGCCTCCGCTTTCCTCTCTATGGGCAGTCGGTGA TTTCACCTTCAGAAGTCACAGAATGATTTT | 18 |
|  | CCACTACGCCTCCGCTTTCCTCTCTATGGGCAGTCGGTGA TTAAAAAGCCATTTGACCGTGGAG | 19 |
|  | CCACTACGCCTCCGCTTTCCTCTCTATGGGCAGTCGGTGA TTCTATATGTAGAGGCTGTTGGAAGCTG | 20 |
|  | CCACTACGCCTCCGCTTTCCTCTCTATGGGCAGTCGGTGA TTCATACTTACCATGCCACTTTCCCTT | 21 |
|  | CCACTACGCCTCCGCTTTCCTCTCTATGGGCAGTCGGTGA TTAGATTGCACCGGTCGACAAA | 22 |
|  | CCACTACGCCTCCGCTTTCCTCTCTATGGGCAGTCGGTGA TTCACCAGCGTGTCCAGGAA | 23 |
|  | CCACTACGCCTCCGCTTTCCTCTCTATGGGCAGTCGGTGA TTTCCACCATGACTTTGAGGTTGAG | 24 |
|  | CCACTACGCCTCCGCTTTCCTCTCTATGGGCAGTCGGTGA TTACTGTTTCGTATTTATAGCTGATTTGATGGA | 25 |
|  | CCACTACGCCTCCGCTTTCCTCTCTATGGGCAGTCGGTGA TTACGTCTTCCTTCTCTCTCTGTCA | 26 |
|  | CCACTACGCCTCCGCTTTCCTCTCTATGGGCAGTCGGTGA TTGACTATGTCCGGGAACACAAAGA | 27 |

Notes:
(1) the underlined portion of the sequence of the first linker is the first tag sequence for labelling a distinct sample, the "N" portion is the second tag sequence for labelling a distinct target molecular sequence, and the other portion is the fixed sequence of the first linker for subsequent PCR amplification (except the three bases adjacent to the first tag sequence); (2) the underlined portion of the sequence of the third primer is the target-region-specifically-binding sequence at the 3' end, and the other portion is the fixed sequence of the third primer at the 5' end; and (3) all sequences are shown from 5' to 3'.

The particular experimental process of this example is as follows:

1. DNA from a peripheral blood tumor cell sample (100 ng) was end repaired, then connected with linkers having particular sequences (the first linker and the second linker) by means of blunt end connection or sticky end connection, and then amplified in 5 to 7 cycles. One of the primers (the first primer) for PCR amplification harbored a biotin modification or another label that allows for separation of a particular strand.

1.1 The reaction system for end repairing is as shown in Table 2 below. Reaction was allowed at 20° C. for 30 min.

TABLE 2

| Component | Usage amount |
|---|---|
| Fragmented DNA | X (100 ng) |
| T4DNA polymerase (NEB Corporation) | 5 |
| T4PNK (NEB Corporation) | 5 |
| dNTP mixture | 1.6 |
| T4PNK buffer (NEB Corporation) (10×) | 10 |
| Total amount | 100 |

1.2 The connection reaction system is as shown in Table 3 below. Reaction was allowed at 20° C. for 30 min.

TABLE 3

| Component | Usage amount |
|---|---|
| DNA after end repairing | X |
| T4DNA polymerase (NEB Corporation) | 1 |
| T4DNA ligase buffer (NEB Corporation) | 5 |
| First linker | 5 |
| Second linker | 5 |
| ddH$_2$O | Balance |
| Total amount | 50 |

1.3 The PCR amplification system is as shown in Table 4 below:

TABLE 4

| Component | Usage amount |
|---|---|
| DNA connection product | X |
| dNTP (25 mM) | 3 |
| Platinum pfx DNA polymerase (Life Technology) | 0.6 |
| First primer | 3 |
| Second primer | 3 |
| MgSO$_4$ | 4 |
| 10 × pfx buffer | 10 |
| ddH$_2$O | Balance |
| Total amount | 100 |

The PCR amplification process is as shown in Table 5 below:

TABLE 5

| Temperature | Time | Cycle |
|---|---|---|
| 72° C. | 20 min | 1 |
| 95° C. | 5 min | 1 |
| 95° C. | 30 s | 7 |
| 58° C. | 30 s |  |
| 70° C. | 1 min |  |
| 72° C. | 5 min | 1 |
| 4° C. | ∞ | 1 |

2. One (1) pmol of the above PCR amplification product connected with the particular linkers (the first linker and the second linker) was removed, and single-stranded DNA was captured using a streptavidin magnetic bead. Elution with 0.1 M NaOH was employed during the single strand capture process.

3. The biotin-labelled single strand of the PCR amplification product captured above was subjected to linear amplification using a single primer (the third primer) adapted for binding to the target region. The linear amplification system and process are respectively as shown in Table 6 and Table 7 below:

TABLE 6

| Component | Usage |
|---|---|
| Captured single-stranded DNA | 6 |
| 5 × Ion AmpliSeq™ HiFi Mix (Life Technology) | 4 |
| Third primer | 10 |
| Total amount | 20 |

TABLE 7

| Temperatur | Time | Cycle |
|---|---|---|
| 95° C. | 3 min | 1 |
| 95° C. | 30 s | 40 |
| 65° C. | 1 min | |
| 70° C. | 5 min | 1 |

4. The product from the linear amplification was subjected to multiplex exponential amplification. The upstream primer of the amplification primers was the primer specifically binding to the biotin-labeled strand in the PCR amplification system in step 1.3 above (the first primer), and the downstream primer was the primer set in the linear amplification (the third primer). The system and process of the multiplex exponential amplification are as shown in Table 8 and Table 9 below:

TABLE 8

| Component | Usage |
|---|---|
| Linear amplified DNA | 6 |
| 5 × Ion AmpliSeq™ HiFi Mix (Life Technology) | 4 |
| First primer and third primer | 10 |
| Total amount | 20 |

TABLE 9

| Temperatur | Time | Cycle |
|---|---|---|
| 95° C. | 3 min | 1 |
| 95° C. | 30 s | 20 |
| 65° C. | 1 min | |
| 70° C. | 5 min | 1 |

5. Finally, the product from the multiplex exponential amplification was purified and then subjected to sequencing analysis on an instrument. The analysis included enrichment percentage of the target region, homogeneity of coverage, variation, and the like. The results are as shown in Table 10 below:

TABLE 10

| Parameter | Value |
|---|---|
| Sample | Peripheral blood tumor cell sample |
| Total number of reads | 1253091 |
| Number of targets | 1009600 |
| Percentage of targets | 80.56% |
| Coverage rate of targets | 99.97% |
| Capturing efficiency of target regions | 66% |
| Number of single base mutation | 43893 |

Notes: Total number of reads refers to the total number of reads read by sequencing; number of targets refers to the total number of reads read in the target regions; percentage of targets refers to the ratio of the total number of target regions to the total number of reads; coverage rate of targets refers to the ratio of the target regions covered; capturing efficiency of target regions refers to the ratio of the target regions captured to the target regions in the whole reference genome; and number of single base mutation refers to the number of single base mutation detected in the target regions.

The present application further provides another example as shown below to demonstrate the feasibility of the method of the present invention. Except that a lung cancer sample was substituted for the peripheral blood tumor cell sample, this example was the same as the example above in other aspects, including the experimental process and the materials. The results are as shown in Table 11 below:

TABLE 11

| Parameter | Value |
|---|---|
| Sample | Lung cancer sample |
| Total number of reads | 3163794 |
| Average sequencing depth | 32204.13 |
| Coverage rate of targets | 100.00% |
| Capturing efficiency of target regions | 89.10% |

Table 12 shows the results of allele frequency obtained by a conventional hybridization capture method and the method for enriching a target region based on multiplex PCR according to the present invention.

TABLE 12

| Lung cancer sample | | | | | Conventional hybridization capture method | Enriching method based on multiplex PCR |
|---|---|---|---|---|---|---|
| Gene position | Gene sequence | Gene type | Variation | Gene | Allele frequency | Allele frequency |
| chr7: 55242469 | TTAAGAGA AGCAACAT CTC | TTAAG AGAAG CAACA TCTC/T | INDEL | EGFR | 0.18539728 | 0.27706 |

The results in Table 11 and Table 12 indicate that the method for enriching a target region based on multiplex PCR according to the present invention had a capturing efficiency of target regions of up to 89.10%, and could detect the same result as the conventional hybridization capture method, with the frequency being substantially similar and the result being consistent. Hence, it can be confirmed that the method of the present invention can be used for enriching target regions.

The disclosure set forth above is intended to describe the present invention in further detail by reference to particular embodiments, and is not to be construed as limiting the practical implementation of the present invention thereto. A number of simple deductions or substitutions could be made by a person of ordinary skill in the art to which the present invention pertains without departing from the concept of the present invention.

What is claimed is:

1. A method for enriching for a target region based on multiplex PCR, comprising the following steps:
connecting a first linker and a second linker respectively to a terminal end of a nucleic acid fragment comprising a target region to be enriched under the action of a ligase to obtain a linker-connected product, wherein the first linker comprises a fixed sequence of the first linker for subsequent PCR amplification, a first tag sequence for labeling a distinct sample and a second tag sequence for labeling a distinct target molecular sequence, the first linker and the second linker are both short double-stranded nucleotide sequences, and the nucleic acid fragment is a double-stranded nucleic acid fragment;
PCR amplifying the linker-connected product with a first primer that specifically binds to the fixed sequence of the first linker and a second primer that specifically binds to the second linker to obtain an amplification product, wherein the first primer has a first affinity label;
capturing a single strand of the amplification product harboring the first affinity label via a solid-phase support, wherein the solid-phase support carries a second affinity label capable of affinity binding to the first affinity label;
performing single-primer linear amplification with a third primer using the captured single strand as template, wherein the third primer comprises a fixed sequence of the third primer at the 5' end and a target-region-specifically-binding sequence at the 3' end; and performing exponential amplification with the third primer and the first primer using a linear amplification product as template to obtain a product comprising the target region.

2. The method for enriching for a target region based on multiplex PCR according to claim 1, wherein the first tag sequence is a sequence with a length of 5 to 10 bases, and the second tag sequence is a random sequence with a length of 10 to 12 bases.

3. The method for enriching for a target region based on multiplex PCR according to claim 1, wherein the nucleic acid fragment comprising the target region to be enriched is a nucleic acid fragment having been end repaired.

4. The method for enriching for a target region based on multiplex PCR according to claim 1, wherein the first affinity label is a biotin label, the second affinity label is a streptavidin label, and the solid-phase support is a magnetic bead.

* * * * *

SEQUENCE LISTING

<160> NUMBER OF SEQ ID NOS: 27

<210> SEQ ID NO 1
<211> LENGTH: 53
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (31)..(40)
<223> OTHER INFORMATION: n is a, c, g, or t

<400> SEQUENCE: 1
ccatctcatc cctgcgtgtc tccgactcag nnnnnnnnnn ctaaggtaac gat        53

<210> SEQ ID NO 2
<211> LENGTH: 55
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (14)..(23)
<223> OTHER INFORMATION: n is a, c, g, or t

<400> SEQUENCE: 2
atcgttacct tagnnnnnnn nnnctgagtc ggagacacgc aggatgaga tggtt        55

<210> SEQ ID NO 3
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 3
aagtcggagg ccaagcggtc ttagga                                      26

<210> SEQ ID NO 4
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 4
tcctaagacc gcttggcctc cgact                                       25

<210> SEQ ID NO 5
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: biotin modification
<222> LOCATION: (1)..(1)

<400> SEQUENCE: 5
ccatctcatc cctgcgtgtc                                             20

<210> SEQ ID NO 6
<211> LENGTH: 25
<212> TYPE: DNA
<213> ORGANISM: Artificial Sequence
<220> FEATURE:

<223> OTHER INFORMATION: Synthetic Sequence

<400> SEQUENCE: 6
tcctaagacc gcttggcctc cgact     25

<210> SEQ ID NO 7
<211> LENGTH: 63
<212> TYPE: DNA
<213> ORGANISM: Artificial Sequence
<220> FEATURE:
<223> OTHER INFORMATION: Synthetic Sequence

<400> SEQUENCE: 7
ccactacgcc tccgctttcc tctctatggg cagtcggtga tttctatggt gtgtccccca     60 act     63

<210> SEQ ID NO 8
<211> LENGTH: 63
<212> TYPE: DNA
<213> ORGANISM: Artificial Sequence
<220> FEATURE:
<223> OTHER INFORMATION: Synthetic Sequence

<400> SEQUENCE: 8
ccactacgcc tccgctttcc tctctatggg cagtcggtga ttgggagccc ccgttctata     60 tca     63

<210> SEQ ID NO 9
<211> LENGTH: 63
<212> TYPE: DNA
<213> ORGANISM: Artificial Sequence
<220> FEATURE:
<223> OTHER INFORMATION: Synthetic Sequence

<400> SEQUENCE: 9
ccactacgcc tccgctttcc tctctatggg cagtcggtga ttgcgccaca gagaagttgt     60 tga     63

<210> SEQ ID NO 10
<211> LENGTH: 64
<212> TYPE: DNA
<213> ORGANISM: Artificial Sequence
<220> FEATURE:
<223> OTHER INFORMATION: Synthetic Sequence

<400> SEQUENCE: 10
ccactacgcc tccgctttcc tctctatggg cagtcggtga tttctctcgg aggaaggact     60 tgag     64

<210> SEQ ID NO 11
<211> LENGTH: 64
<212> TYPE: DNA
<213> ORGANISM: Artificial Sequence
<220> FEATURE:
<223> OTHER INFORMATION: Synthetic Sequence

<400> SEQUENCE: 11
ccactacgcc tccgctttcc tctctatggg cagtcggtga ttgagagaac gcggaattgg     60 tcta     64

<210> SEQ ID NO 12
<211> LENGTH: 70

<212> TYPE: DNA
<213> ORGANISM: Artificial Sequence
<220> FEATURE:
<223> OTHER INFORMATION: Synthetic Sequence

<400> SEQUENCE: 12
ccactacgcc tccgctttcc tctctatggg cagtcggtga ttttcattat catctttgtc    60
atcagctgaa                                                          70

<210> SEQ ID NO 13
<211> LENGTH: 64
<212> TYPE: DNA
<213> ORGANISM: Artificial Sequence
<220> FEATURE:
<223> OTHER INFORMATION: Synthetic Sequence

<400> SEQUENCE: 13
ccactacgcc tccgctttcc tctctatggg cagtcggtga ttagcccag tgatcttcca     60 gata                                                                64

<210> SEQ ID NO 14
<211> LENGTH: 74
<212> TYPE: DNA
<213> ORGANISM: Artificial Sequence
<220> FEATURE:
<223> OTHER INFORMATION: Synthetic Sequence

<400> SEQUENCE: 14
ccactacgcc tccgctttcc tctctatggg cagtcggtga ttttaaatac agaaggcata    60
aatattccag caga                                                     74

<210> SEQ ID NO 15
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 15
ccactacgcc tccgctttcc tctctatggg cagtcggtga tttgctattc tcagatgact    60
ctgtgttttt                                                          70

<210> SEQ ID NO 16
<211> LENGTH: 68
<212> TYPE: DNA
<213> ORGANISM: Artificial Sequence
<220> FEATURE:
<223> OTHER INFORMATION: Synthetic Sequence

<400> SEQUENCE: 16
ccactacgcc tccgctttcc tctctatggg cagtcggtga ttgtgtttga ctctagatgc    60
tgtgagaa                                                            68

<210> SEQ ID NO 17
<211> LENGTH: 63
<212> TYPE: DNA
<213> ORGANISM: Artificial Sequence
<220> FEATURE:
<223> OTHER INFORMATION: Synthetic Sequence

<400> SEQUENCE: 17
ccactacgcc tccgctttcc tctctatggg cagtcggtga ttgctcatac agcaggccat    60

-continued aga                                                                63

<210> SEQ ID NO 18
<211> LENGTH: 70
<212> TYPE: DNA
<213> ORGANISM: Artificial Sequence
<220> FEATURE:
<223> OTHER INFORMATION: Synthetic Sequence

<400> SEQUENCE: 18
ccactacgcc tccgctttcc tctctatggg cagtcggtga tttcaccttc agaagtcaca    60
gaatgatttt                                                         70

<210> SEQ ID NO 19
<211> LENGTH: 64
<212> TYPE: DNA
<213> ORGANISM: Artificial Sequence
<220> FEATURE:
<223> OTHER INFORMATION: Synthetic Sequence

<400> SEQUENCE: 19
ccactacgcc tccgctttcc tctctatggg cagtcggtga ttaaaaagcc atttgaccgt    60
ggag                                                               64

<210> SEQ ID NO 20
<211> LENGTH: 68
<212> TYPE: DNA
<213> ORGANISM: Artificial Sequence
<220> FEATURE:
<223> OTHER INFORMATION: Synthetic Sequence

<400> SEQUENCE: 20
ccactacgcc tccgctttcc tctctatggg cagtcggtga ttctatatgt agaggctgtt    60
ggaagctg                                                           68

<210> SEQ ID NO 21
<211> LENGTH: 67
<212> TYPE: DNA
<213> ORGANISM: Artificial Sequence
<220> FEATURE:
<223> OTHER INFORMATION: Synthetic Sequence

<400> SEQUENCE: 21
ccactacgcc tccgctttcc tctctatggg cagtcggtga ttcatactta ccatgccact    60
ttccctt                                                            67

<210> SEQ ID NO 22
<211> LENGTH: 62
<212> TYPE: DNA
<213> ORGANISM: Artificial Sequence
<220> FEATURE:
<223> OTHER INFORMATION: Synthetic Sequence

<400> SEQUENCE: 22
ccactacgcc tccgctttcc tctctatggg cagtcggtga ttagattgca ccggtcgaca    60
aa                                                                 62

<210> SEQ ID NO 23
<211> LENGTH: 60
<212> TYPE: DNA
<213> ORGANISM: Artificial Sequence
<220> FEATURE:
<223> OTHER INFORMATION: Synthetic Sequence

```
<400> SEQUENCE: 23
ccactacgcc tccgctttcc tctctatggg cagtcggtga ttcaccagcg tgtccaggaa    60

<210> SEQ ID NO 24
<211> LENGTH: 65
<212> TYPE: DNA
<213> ORGANISM: Artificial Sequence
<220> FEATURE:
<223> OTHER INFORMATION: Synthetic Sequence

<400> SEQUENCE: 24
ccactacgcc tccgctttcc tctctatggg cagtcggtga tttccaccat gactttgagg    60
ttgag                                                                65

<210> SEQ ID NO 25
<211> LENGTH: 73
<212> TYPE: DNA
<213> ORGANISM: Artificial Sequence
<220> FEATURE:
<223> OTHER INFORMATION: Synthetic Sequence

<400> SEQUENCE: 25
ccactacgcc tccgctttcc tctctatggg cagtcggtga ttactgtttc gtatttatag    60
ctgatttgat gga                                                       73

<210> SEQ ID NO 26
<211> LENGTH: 65
<212> TYPE: DNA
<213> ORGANISM: Artificial Sequence
<220> FEATURE:
<223> OTHER INFORMATION: Synthetic Sequence

<400> SEQUENCE: 26
ccactacgcc tccgctttcc tctctatggg cagtcggtga ttacgtcttc cttctctctc    60
tgtca                                                                65

<210> SEQ ID NO 27
<211> LENGTH: 65
<212> TYPE: DNA
<213> ORGANISM: Artificial Sequence
<220> FEATURE:
<223> OTHER INFORMATION: Synthetic Sequence

<400> SEQUENCE: 27
ccactacgcc tccgctttcc tctctatggg cagtcggtga ttgactatgt ccgggaacac    60
aaaga                                                                65
```